A

United States Patent
Ono et al.

(10) Patent No.: US 6,878,827 B2
(45) Date of Patent: Apr. 12, 2005

(54) PROCESS FOR PRODUCING ANHYDRIDE OF AMINOTHIAZOLE DERIVATIVE

(75) Inventors: Hiroki Ono, Osaka (JP); Masaru Hayashi, Osaka (JP); Masaru Ohnishi, Osaka (JP); Kazuo Ohkawa, Osaka (JP); Masato Kitayama, Osaka (JP)

(73) Assignee: Fujisawa Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 10/432,605

(22) PCT Filed: Nov. 28, 2001

(86) PCT No.: PCT/JP01/10356

§ 371 (c)(1),
(2), (4) Date: Jun. 3, 2003

(87) PCT Pub. No.: WO02/46175

PCT Pub. Date: Jun. 13, 2002

(65) Prior Publication Data

US 2004/0034233 A1 Feb. 19, 2004

(30) Foreign Application Priority Data

Dec. 4, 2000 (JP) ........................................ 2000-368319

(51) Int. Cl.$^7$ ............................................. C07D 277/56
(52) U.S. Cl. ........................................................ 548/194
(58) Field of Search ................................. 548/195, 194; 562/892, 887

(56) References Cited

U.S. PATENT DOCUMENTS 1,961,542 A * 6/1934 Al ............................... 562/892
4,426,528 A   1/1984 Burchfield
4,754,031 A   6/1988 Angerbauer et al.
2002/0198375 A1 * 12/2002 Colberg et al. ............. 540/220

FOREIGN PATENT DOCUMENTS

JP   02-53782   2/1990

* cited by examiner

Primary Examiner—Johann Richter
Assistant Examiner—Ebenezer Sackey
(74) Attorney, Agent, or Firm—Oblon, Spivak, McClelland, Maier & Neustadt, P.C.

(57) ABSTRACT

This invention provides a novel industrial process for preparation of an anhydride of 2-(2-aminothiazole-4-yl)-2-hydroxy compound.

5 Claims, No Drawings

PROCESS FOR PRODUCING ANHYDRIDE OF AMINOTHIAZOLE DERIVATIVE

This invention relates to a novel process for preparation of aminothiazole-4-yl)-2-hydroxy compound in anhydrous form. More particularly, this invention relates to a novel process for preparation of 2-(2-aminothiazole-4-yl)-2-hydroxy compound in anhydrous form from hydrate of the 2-(2-aminothiazole-4-yl)-2-hydroxy compound represented by the following general formula in high yields:

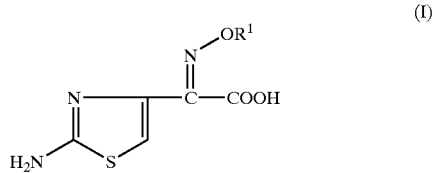

in which $R^1$ is acyl, protected carboxy(lower)alkyl or alkyl.

An aminothiazole derivative usually has one or two molecules of crystal water. This invention is intended to efficiently eliminate crystal water that becomes hindrance when synthesizing acid chloride of aminothiazole derivative.

Accordingly, this invention is intended to provide a novel industrial process for preparation of the 2-(2-aminothiazole-4-yl)-2-hydroxy compound in anhydrous form.

Conventionally, acid chloride was synthesized by using hydrate of the 2-(2-aminothiazole-4-yl)-2-hydroxy compound (I). In this synthesis, however, it is necessary to use a halogenation agent amounting to an equivalent corresponding to 1 or 2 molecules of the crystal water. Usually, the halogenation agent amounting to approximately 3 equivalents was used. In this invention, the amount of the use of the halogenation agent was able to be reduced to approximately 1 to 1.2 equivalents by eliminating the crystal water of the compound (I) to obtain the compound (I) in anhydrous form. By reducing the amount of the use of the halogenation agent, an environmental load can be reduced.

The inventors of this invention earnestly studied processes for industrial preparation of the 2-(2-aminothiazole-4-yl)-2-hydroxy compound, and eventually succeeded in completing a novel preparation process capable of easily eliminating the crystal water from the crystal-water-including crystal of the 2-(2-aminothiazole-4-yl)-2-hydroxy compound.

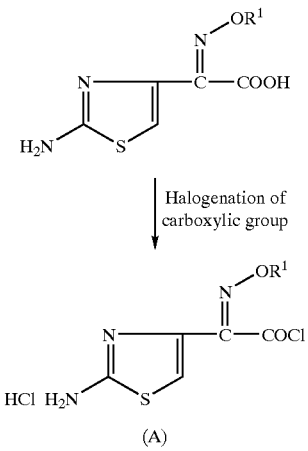

The 2-(2-aminothiazole-4-yl)-2-hydroxy compound (I) in anhydrous form, obtained by the preparation process of this invention, reacts with a halogenation agent, such as phosphorus pentachloride, and further reacts as acid chloride hydrochloride (A) with 7-aminocephalo compound, thereby preventing the growth of various pathogenic microbes, such as Gram-positive bacteria and Gram-negative bacteria. The compound is therefore useful in obtaining antibacterial agents.

Suitable examples and explanations of $R^1$ described above in this specification are described below in detail.

Suitable "acyl group" may include aliphatic acyl and acyl including an aromatic ring or heterocyclic ring. Suitable examples of the acyl group may include lower alkanoyl, for example, formyl, acetyl, propionyl, butyryl, isobutyl, valeryl, isovaleryl, oxalyl, succinyl, pivaloyl, etc.;

lower alkoxycarbonyl, for example, methoxycarbonyl, 1-cyclopropylethoxycarbonyl, isopropoxycarbonyl, butoxycarbonyl, t-butoxycarbonyl, pentyloxycarbonyl, hexyloxycarbonyl, etc.;

lower alkanesulfonyl, for example, mesyl, ethanesulfonyl, propanesulfonyl, 1-methylethanesulfonyl, butanesulfonyl, etc.;

arenesulfonyl, for example, benzensulfonyl, tosyl, etc.;

aroyl, for example, benzoyl, toluoyl, xyloyl, naphthoyl, phthaloyl, indancarbonyl, etc.; and ar(lower)alkoxycarbonyl, for example, phenylacetyl, phenylpropionyl, etc.

The acyl moiety may have at least one suitable substituent, such as halogen, for example, chlorine, bromine, fluorine or iodine.

Suitable "protected carboxy(lower)alkyl" may include, for example, esterified carboxy(lower)alkyl, more preferably, lower alkoxycarbonyl(lower)alkyl, for example, methoxycarbonylmethyl, t-butoxycarbonylethyl, etc.; mono-, di- or triphenyl(lower)alkoxycarbonyl(lower)alkyl, for example, benzhydryloxycarbonylmethyl, etc.; mono-, di- or trichloro(lower)alkoxycarbonyl(lower)alkyl, for example, chloromethoxycarbonylmethyl, 2-iodoethoxycarbonylmethyl, etc.

Suitable "lower alkyl" may include methyl, ethyl, etc.

The process for preparation of the object compound (I) of this invention will be described below in detail.

Process 1

After the crystal water of the compound (I) is refluxed or suspended under heating in a ketone solution, such as acetone, methylethylketone or methylisobutylketone, or acetonitrile, its crystal is filtered and dried under reduced pressure to obtain a crystal not including the crystal water.

This invention will be described below in accordance with the following Preparations and Examples.

Preparation 1-(1)

Ethyl 2-(2-aminothiazole-4-yl)-2-hydroxyiminoacetate (syn-isomer) (24.0 g) was suspended in ethanol (26 ml), and 1N aqueous sodium hydroxide (125 ml) was added dropwise thereto for one hour under stirring at 45° C. After the dropwise addition, the mixture was stirred for two hours at the same temperature. The reaction mixture was cooled to 5° C. and stirred for one hour. The precipitate was filtered and collected, washed with ethanol, and dried under vacuum to obtain 2-(2-aminothiazole-4-yl)-2-hydroxyiminoacetate sodium dihydrate (syn-isomer) (24.6 g).

mp: 130–131° C. (decomposition)
IR (Nujol): 3520, 3300, 1600, 1530 cm$^{-1}$
NMR (DMSO-$d_6$, δ): 6.97 (2H, br s), 7.33 (1H, s)

Preparation 1-(2)

2-(2-aminothiazole-4-yl)-2-hydroxyiminoacetate sodium dihydrate (syn-isomer) (24.6 g) was added to water (160 ml) and stirred at 20 to 30° C. Acetic anhydride (28.7 g) was added dropwise thereto for 60 minutes. During the dropwise addition, the pH of the mixture was controlled to 6.0±0.2 by using 20% aqueous sodium carbonate. After the dropwise addition, the mixture was stirred for 30 minutes, and the pH of the mixture was adjusted to 2.5 by using 6N hydrochloric acid. After the reaction liquid was cooled to 5° C., the precipitated crystal was filtered and washed with isopropanol and acetone successively. The obtained wet crystal was dried under reduced pressure to obtain 2-(2-aminothiazole-4-yl)-2-acetoxyiminoacetic acid (syn-isomer) (23.9 g) including two molecules of crystal water.

IR (Nujol): 3400, 3100, 1760, 1630 cm$^{-1}$

NMR (DMSO-d$_6$, δ): 2.16 (3H, s), 7.21 (1H, s)

Moisture: 14%

EXAMPLE 1

2-(2-aminothiazole-4-yl)-2-acetoxyiminoacetic acid dihydrate (syn-isomer) (20.0 g) was suspended in acetone (200 ml) and stirred, and heated and refluxed at 55 to 56° C. for one hour. After the mixture was cooled to 5° C., the crystal was filtered and washed with acetone, and dried under reduced pressure to obtain 2-(2-aminothiazole-4-yl)-2-acetoxyiminoacetic acid anhydrous crystal (16.4 g).

IR (Nujol): 3400, 3100, 1750, 1600 cm$^{-1}$

NMR (DMSO-d$_6$, δ): 2.16 (3H, s), 7.21 (1H, s)

Moisture: 0.5%

Powder X-ray diffraction (peak angle: 2θ): having X-ray diffraction image having diffraction peaks at 2θ=about 14.7°, about 16.0°, about 19.0°, about 19.5°, about 20.5°, about 21.4°, about 24.5°, about 25.5°, about 25.8°, about 27.2° and about 30.2°, and not having diffraction peaks at about 8.9°, about 14.3°, about 15.3°, about 17.2°, about 18.4°, about 19.6°, about 21.0°, about 22.3°, about 24.3°, about 26.7°, about 27.5°, about 28.5° and about 29.0°

Preparation 2

4-chloro-2-(methoxycarbonylmethoxyimino)-3-oxobutyric acid (200 g) was added to water (400 ml), and suspended and stirred at 5° C. The crystal was dissolved by using sodium hydrogencarbonate (71.2 g). Thiourea (70.5 g) was added, and reaction was performed for 60 minutes at 30° C. while keeping the pH at 5.5 by using aqueous ammonia. After the pH was adjusted to 2 by using dilute hydrochloric acid, the mixture was cooled to 5° C. and stirred for 30 minutes. The precipitated crystal was filtered and collected, and washed with cold water, and then dried under reduced pressure to obtain 2-(2-aminothiazole-4-yl)-2-methoxycarbonylmethoxy iminoacetic acid monohydrate (syn-isomer) (225.2 g) (96.5% yield).

IR (Nujol): 3400, 1770, 1740, 1660, 1610 cm$^{-1}$

NMR (DMSO-d$_6$, δ): 3.68 (3H, s), 4.72 (2H, s), 6.87 (1H, s), 7.26 (2H, s)

KF method (moisture): 6.7%

EXAMPLE 2

2-(2-aminothiazole-4-yl)-2-methoxycarbonylmethoxyimino acetic acid monohydrate (syn-isomer) (10.0 g) was suspended and stirred in acetone (100 ml), and heated and refluxed for 120 minutes. The precipitated crystal was filtered and collected, and dried under reduced pressure to obtain anhydrous 2-(2-aminothiazole-4-yl)-2-methoxycarbonylmethoxyiminoacetic acid (syn-isomer) (9.0 g) (96% yield).

IR (Nujol): 3350, 1760, 1740, 1655 cm$^{-1}$

NMR (DMSO-d$_6$, δ): 3.68 (3H, s), 4.72 (2H, s), 6.87 (1H, s), 7.26 (2H, s)

KF method (moisture): 0.5%

Furthermore, the end product was obtained at high yields in accordance with the following reference examples.

REFERENCE EXAMPLE 1-(1)

2-(2-aminothiazole-4-yl)-2-acetoxyiminoacetic acid anhydrous crystal (syn-isomer) (12.5 g) was suspended and stirred in methylene chloride (125 ml), and cooled to −20 to −25° C. Phosphorus pentachloride (13.6 g) was added thereto, and reaction was performed for 15 hours at the same temperature. The precipitated crystal was filtered, washed with methylene chloride, and dried under reduced pressure to obtain 2-(2-aminothiazole-4-yl)-2-acetoxyiminoacetyl chloride hydrochloride (syn-isomer) (14.6 g).

mp: 128–130° C. (decomposition)

IR (Nujol): 3300, 1800, 1780, 1640, 1590 cm$^{-1}$

REFERENCE EXAMPLE 1-(2)

7-amino-3-vinyl-3-cephem-4-carboxylic acid (4.52 g) and 1,3-bistrimethylsilylurea (10.2 g) was suspended in ethyl acetate ester (80 ml), heated and refluxed for 120 minutes, and then silylated and dissolved. The reaction liquid was cooled to −20° C., and 2-(2-aminothiazole-4-yl)-2-acetoxyiminoacetyl chloride hydrochloride (syn-isomer) (6.25 g) was added thereto, and reaction was performed for 30 minutes. Cold water (90 ml) was added to the reaction liquid, and the produced precipitate was filtered and collected, washed with cold water, and dried under reduced pressure to obtain 7-[2-(2-aminothiazole-4-yl)-2-acetoxyiminoacetamide]-3-vinyl-3-cephem-4-carboxylic acid (syn-isomer) (8.32 g) (95% yield).

IR (Nujol): 3250, 1770, 1750, 1705, 1650, 1590, 1540 cm$^{-1}$

NMR (DMSO-d$_6$, δ): 2.33 (3H, s), 3.60, 3.87 (2H, Abq, J=18 Hz), 5.23 (1H, d, J=10 Hz), 5.60 (1H, d, J=17 Hz), 58.2 (1H, dd, J=8 Hz, J=5 Hz), 6.92 (1H, dd, J=10 Hz, J=17 Hz), 7.17 (1H, s), 9.97 (1H, d, J=8 Hz)

REFERENCE EXAMPLE 1-(3)

7-[2-(2-aminothiazole-4-yl)-2-acetoxyiminoacetamide]-3-vinyl-3-cephem-4-carboxylic acid (syn-isomer) (1.3 g) was suspended in water (13 ml) and stirred at 5° C. The crystal was dissolved by using aqueous sodium carbonate, and ammonium chloride (670 mg) was added thereto. By using aqueous sodium carbonate, the pH was adjusted to 8.5, and reaction was performed for 60 minutes while the same temperature and the same pH were maintained. By using dilute hydrochloric acid, the pH was adjusted to 2.5. The produced precipitate was filtered and collected, washed with cold water, and dried under reduced pressure to obtain 7-[2-(2-aminothiazole-4-yl)-hydroxyiminoacetamide]-3-vinyl-3-cephem-4-carboxylic acid (syn-isomer) (1.12 g) (95% yield).

IR (Nujol): 3300, 1780, 1660, 1605 cm$^{-1}$

NMR (DMSO-d$_6$, δ): 3.53, 3.80 (2H, Abq, J=18 Hz), 5.17 (1H, d, J=5 Hz), 5.28 (1H, D, J=10 Hz), 5.57 (1H, d, J=17 Hz), 5.75 (1H, dd, J=17 Hz, J=10 Hz), 7.07 (2H, br s), 9.42 (1H, d, J=8 Hz), 11.25 (1H, br s)

What is claimed is:

1. A process for preparation of a compound represented by the formula (I) in anhydrous form:

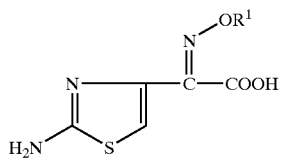

(I)

in which $R^1$ is acyl, protected carboxy(lower)alkyl or alkyl, comprising treating a hydrate of 2-(2-aminothiazole-4-yl)-2-hydroxy compound represented by the formula (I) in a ketone or acetonitrile.

2. The process of claim 1, wherein $R^1$ is acyl.

3. The process of claim 1, wherein $R^1$ is protected carboxy(lower)alkyl.

4. The process of claim 1, wherein $R^1$ is alkyl.

5. The process of claim 1, wherein the hydrate is a syn-isomer.

* * * * *